(12) United States Patent
Alam et al.

(10) Patent No.: US 6,514,204 B2
(45) Date of Patent: Feb. 4, 2003

(54) METHODS FOR ESTIMATING TISSUE STRAIN

(75) Inventors: Sheikh Kaisar Alam, Somerset, NJ (US); Ernest J. Feleppa, Rye, NY (US); Frederic L. Lizzi, Tenafly, NJ (US)

(73) Assignee: Riverside Research Institute, New York, NY (US)

( * ) Notice: Subject to any disclaimer, the term of this patent is extended or adjusted under 35 U.S.C. 154(b) by 0 days.

(21) Appl. No.: 09/910,618

(22) Filed: Jul. 20, 2001

(65) Prior Publication Data

US 2002/0040187 A1 Apr. 4, 2002

Related U.S. Application Data

(60) Provisional application No. 60/219,517, filed on Jul. 20, 2000.

(51) Int. Cl.[7] .............................................. A61B 8/00
(52) U.S. Cl. ........................................................ 600/442
(58) Field of Search ........................ 600/410, 407–471, 600/504, 587, 481; 324/309, 300, 306, 318; 73/625, 626, 587, 787, 818

(56) References Cited

U.S. PATENT DOCUMENTS

| 5,107,837 A | * | 4/1992 | Ophir et al. ............... 600/437 |
| 5,524,636 A | * | 6/1996 | Sarvazyan et al. .......... 600/587 |
| 5,606,971 A | * | 3/1997 | Sarvazyan ................. 600/438 |
| 5,727,561 A | * | 3/1998 | Owsley .................... 600/481 |
| 5,810,731 A | * | 9/1998 | Sarvazyan et al. .......... 600/438 |
| 5,977,770 A | * | 11/1999 | Ehman ..................... 324/318 |
| 6,144,199 A | * | 11/2000 | Sharf et al. ................ 324/300 |
| 6,213,947 B1 | * | 4/2001 | Phillips .................... 600/443 |

* cited by examiner

*Primary Examiner*—Marvin M. Lateef
*Assistant Examiner*—Ali M. Imam
(74) *Attorney, Agent, or Firm*—Baker Botts LLP (57) ABSTRACT

Improved methods of signal processing for generating estimates of tissue strain are presented. These techniques generally employ the frequency shifting of post-compression spectral data to determine a scaling factor which approximates the applied tissue strain. The scaling factor can be determined by finding the maximum correlation between the frequency shifted post-compression data to the pre-compression data and can also be determined by minimizing the variance of the ratio of such data. Correlation tracking and maximum correlation magnitude techniques for improving the results of elastography are also presented.

8 Claims, 8 Drawing Sheets

Precompression

FIG. 8A

Compressed

FIG. 8B

Strain profile

FIG. 8C

METHODS FOR ESTIMATING TISSUE STRAIN

SPECIFICATION

This application claims the benefit of U.S. Provisional application, Ser. No. 60/219,517, entitled Imaging of Radioactive Seeds for Radiation Therapy of the Prostate, filed on Jul. 20, 2000.

BACKGROUND OF THE INVENTION

1. Field of the Invention

This invention relates to ultrasonic elasticity imaging devices and more particularly relates to computer based signal processing methods for improving strain estimation.

2. Description of the Related Art

Ultrasound based elasticity imaging methods produce images that convey information regarding tissue elastic properties, as opposed to information regarding tissue acoustic scattering properties conveyed by conventional b-mode ultrasonograms. One of the ultrasonic elasticity imaging methods is elastography. Elastography produces high resolution elastograms (elastographic images) that quantitatively depict local tissue deformation under quasi-static external compression.

In general terms, elastograms may be generated as follows:

a.) a frame of RF echo signals from tissue is digitized before compression;

b.) a small quasi-static compression is applied on the tissue along the axis of the transducer by a computer controlled fixture;

c.) a second frame of RF frame echo signals is digitized after compression; and d.) the acquired pre-and post-compression RF echoes are analyzed to compute the induced tissue strain.

Figure 8A:
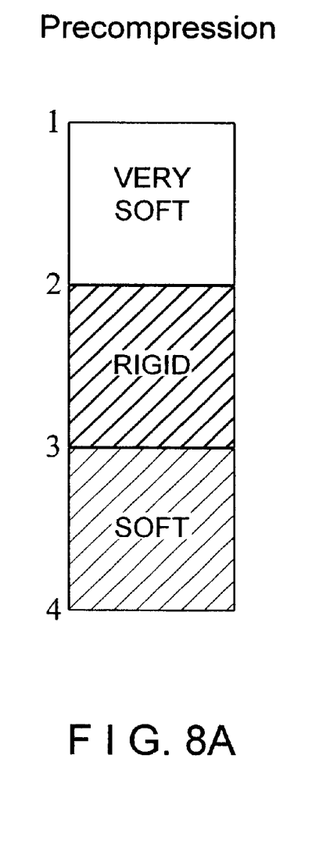
FIG. 8A is a cross sectional view of an exemplary 3-layer object having a soft bottom layer, a rigid middle layer, and a very soft top layer prior to application of a compressive force.
Figure 8B:
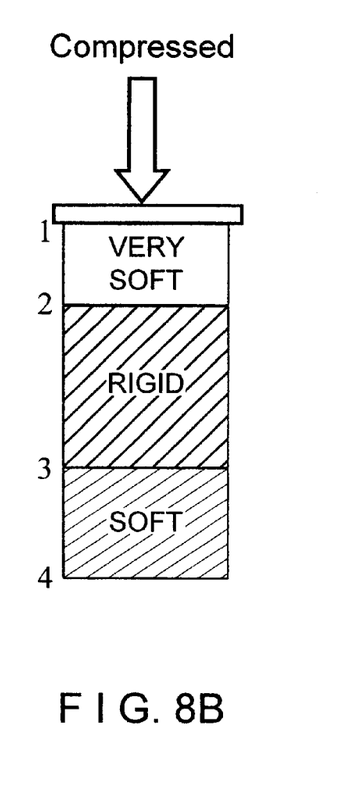
FIG. 8B is a cross sectional view of an exemplary 3-layer object having a soft bottom layer, a rigid middle layer, and a very soft top layer after the application of a compressive force.
Figure 8C:
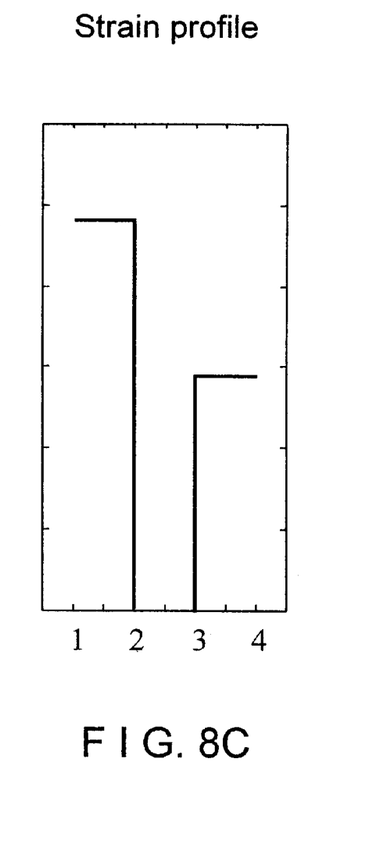
FIG. 8C is a graph illustrating a strain profile of the compressed object of FIG. 1B.

FIGS. 8A through 8C illustrate the principal of elastography. FIGS. 8A and 8B illustrate an exemplary tissue structure which includes a very soft top layer, a rigid intermediate layer and a soft lower layer, before and after compression, respectively. As illustrated in FIG. 8B, when an object is subjected to external compression, the rigid middle layer undergoes virtually no deformation whereas the top softest layer experiences a large deformation. This is represented in the strain profile graph of FIG. 8C. Using suitable signal processing techniques, such a strain profile can be translated into an image of the underlying tissue.

The quality of an elastogram depends largely on the amount and character of undesired motion during signal acquisition as well as the signal processing which determines tissue response when compressed. For example, the quality of elastograms is highly dependent on the quality of time delay estimation (TDE). However, TDE in elastography can be corrupted by two primary factors: the occurrence of random noise, and the large and irregular tissue motions. These motions reduce correlation (decorrelation) between the post-compression signal and the pre-compressed signal.

There have been several attempts to compensate decorrelations that occur at relatively small strains. For example, in I. Céspedes and J. Ophir, *Reduction of signal decorrelation from mechanical compression of tissues by temporal stretching: applications to elastography*, Ultrasound Med. Biol., vol. 23, pp. 95–105 (1997), a temporal stretching method used to compensate for echo waveform changes in the axial direction is disclosed.

Also in the article *An adaptive strain Estimator for Elastography*, by S. K. Alam, J. Ophir, and E. E. Konofagou, IEEE Trans. Ultrason., Ferroelec., Freq. Contr., vol. 45, No. 2, pp. 461–472 (1998), an adaptive stretching strain estimator, which computes strain by iteratively varying a stretch factor to maximize correlation between pre- and post-compression echo signals, is disclosed. While these references provide techniques which allow for compensation of small decorrelations, they suffer from a common drawback in that these techniques cannot produce acceptable elastograms for large and irregular tissue motions.

Accordingly, there remains a need for improved methods of determining tissue strain estimation during compression. An object of the present invention is to provide new and improved signal-processing methods for estimating acceptable tissue strain even in the presence of large tissue motions.

SUMMARY OF THE INVENTION

In accordance with the invention, there is provided a method of estimating tissue strain including transmitting the ultrasonic signals into tissue and detecting first reflected signals. The tissue is then compressed to induce tissue strain. Ultrasonic signals are transmitted into the compressed tissue and second reflected signals are detected. Following detection of the first and second reflected signals, first and second Fourier Transforms of the first and second reflected signals are computed in overlapping temporal windows along each scan line and one of the first and second Fourier Transforms is frequency scaled. A correlation signal of the scaled Fourier Transform and the other Fourier Transform is derived and tissue strain is estimated from the frequency scaling factor representing a maximum of the correlation signal.

In accordance with the invention, there is provided a method of estimating tissue strain which includes transmitting ultrasonic signals into tissue and detecting first reflected signals. The tissue is then compressed to induce tissue strain and ultrasonic signals are transmitted into the compressed tissue and second reflected signals are detected. The first and second reflected signals are converted into the spectral domain and the first and the second reflected signals are low-pass filtered. The second filtered reflected signal is then frequency scaled. A correlation signal of the frequency-scaled filtered reflected signal and the other signal is derived. The tissue strain is finally estimated from the time scaling factor representing a maximum of the correlation function.

In accordance with the invention, there is provided a method of estimating tissue strain which includes transmitting ultrasonic signals into tissue and detecting first reflected signals. The tissue is then compressed to cause tissue strain, ultrasonic signals are transmitted into the compressed tissue and second reflected signals are detected. The first and second reflected signals are transformed into the spectral domain, such as by computing first and second Fourier Transforms of the first and second reflected signals. The second spectral domain signal is frequency scaled by a scaling factor and the variance of the ratio of the scaled spectral domain signal and the non-scaled first spectral domain signal is computed. The scaling factor is then varied and the process repeated to minimize the variance. Local tissue strain is the estimated from the frequency scaling factor representing a minimum of the variance.

DETAILED DESCRIPTION OF PREFERRED EMBODIMENTS

Figure 1:
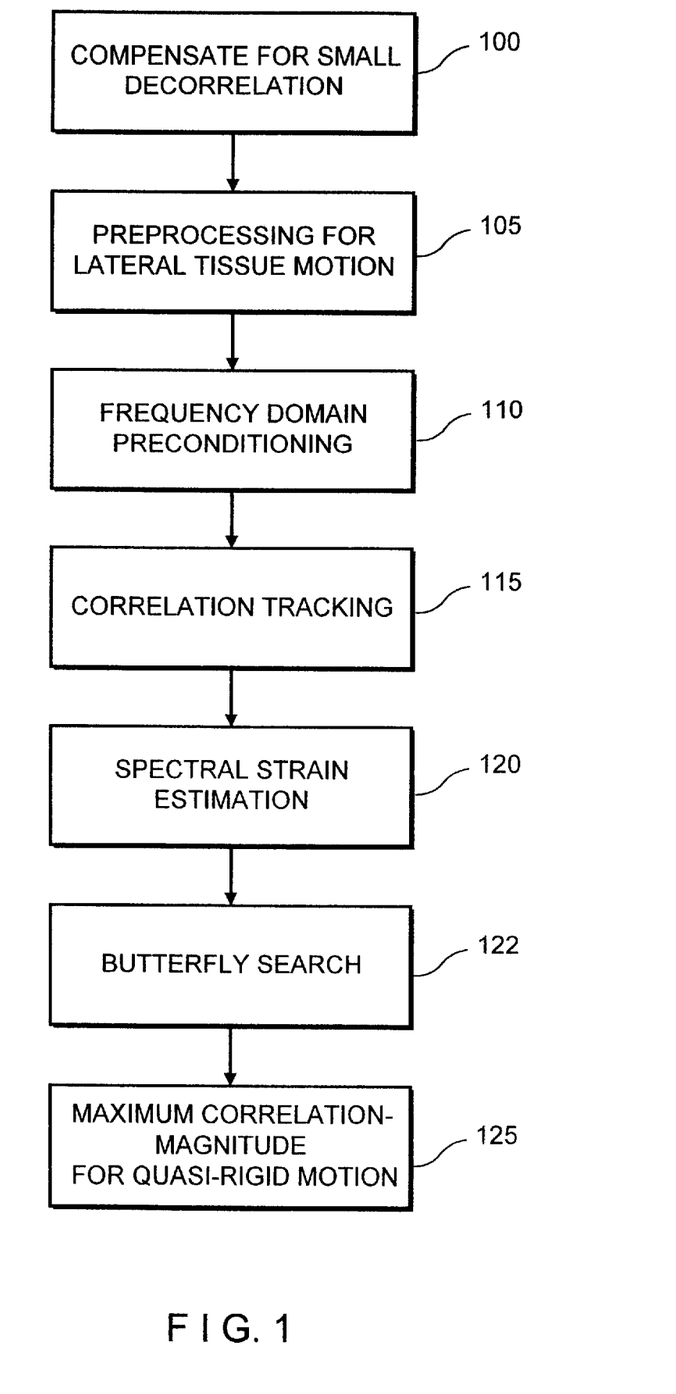
FIG. 1 is a flow-chart providing an overview of a hierarchical processing method for generating tissue strain estimations.

FIG. 1 is a flow chart which illustrates a hierarchical signal processing methodology for providing improved elastograms. It is assumed in this process that pre-compression and post-compression ultrasound data has been acquired in any acceptable manner. Elastograms can first be generated using conventional methods, which can include use of known techniques to compensate for the small decorrelation that occurs even at relatively small strains, such as "temporal stretching" (step 100). In some cases, the conventional methods applied in step 100 do not produce acceptable elastograms, and additional pre-processing can be applied including compensation for lateral tissue-motion (step 105) and frequency-domain pre-conditioning (step 110), which is described in more detail below. The operations of steps 100 through 110 may be sufficient for producing acceptable elastograms in a majority of cases. However, for those cases where the pre-processing method of steps 105 and 110 fail to yield satisfactory results, or where better elastograms are desired, elastograms can be produced using correlation tracking processing (step 115), and if necessary, spectral strain estimation (step 120), the butterfly search method (step 122) or a combination thereof. In the event that processing up to step 120 does not yield an acceptable elastogram, a maximum correlation magnitude processing technique described below can be used to detect regions that exhibit quasi-rigid motion (expected in "stiff" cancers) (step 125). The maximum correlation magnitude processing technique of step 125 does not compute strains directly, but can provide an image corresponding to relative stiffness in tissue and provide reference points for use with other strain-estimation algorithms.

The methods of the present invention generally provide an estimate of strain at one position (local strain). Strain images (elastograms) can be formed from such local strain values by estimating strain throughout a tissue cross-section by segmenting echoes along each scan line into overlapping temporal windows.

The pre-processing for lateral tissue motion of step 105 can be performed using known techniques. One such technique is described by Konofagou et al. in "A new elastographic method for estimation and imaging of lateral displacements, lateral strains, corrected axial strains and Poison's ratios in tissues," Ultrasound Med. Biol., vol. 24, pp. 1183–1199, 1998, which is hereby incorporated by reference in its entirety.

The step of frequency domain preconditioning (step 110) generally involves low pass filtering and generating estimates of the strain using conventional strain-estimation algorithms. It is known that the post-compression data undergoes a degree of frequency scaling with respect to the pre-compression data and that the amount of scaling increases with both frequency and the degree of strain applied. From the use of the low frequency components which result from low pass filtering, rather than the entire spectral bandwidth, the resulting spectrums include smaller frequency shifts and correspondingly smaller RF signal distortions.

It may be shown that the absolute frequency shifting is lower at low frequencies than at high frequencies. For example, if the strain $\epsilon$ is 0.1 (10%), the frequency shift in the Fourier transform of the one-dimensional effective backscatter distribution B is 1 MHz at 10 MHz (0.1*10 MHz=1 MHz), but it is only 0.2 MHz at 2 MHz. Therefore, if only the low frequency components are used rather than the entire bandwidth, only small frequency shifts may result. This, in turn, yields smaller RF signal distortions and may allow conventional strain-estimation methods to perform acceptably. Furthermore, assuming that scatterers have uniformly random positions within a small region-of-interest, $|H(\omega)|$, which represents Fourier Transform of the impulse response of the ultrasonic system, may be estimated using average power spectra. These estimates of $|H(\omega)|$ can be used to determine $B(\omega)$, which represents the Fourier transform of the one-dimensional effective backscatter distribution prior to compression, and $B(\omega/(1-\epsilon))$, which represents the one-dimensional effective backscatter distribution following compression and thereby estimate the resulting tissue strain $\epsilon$.

Figure 2:
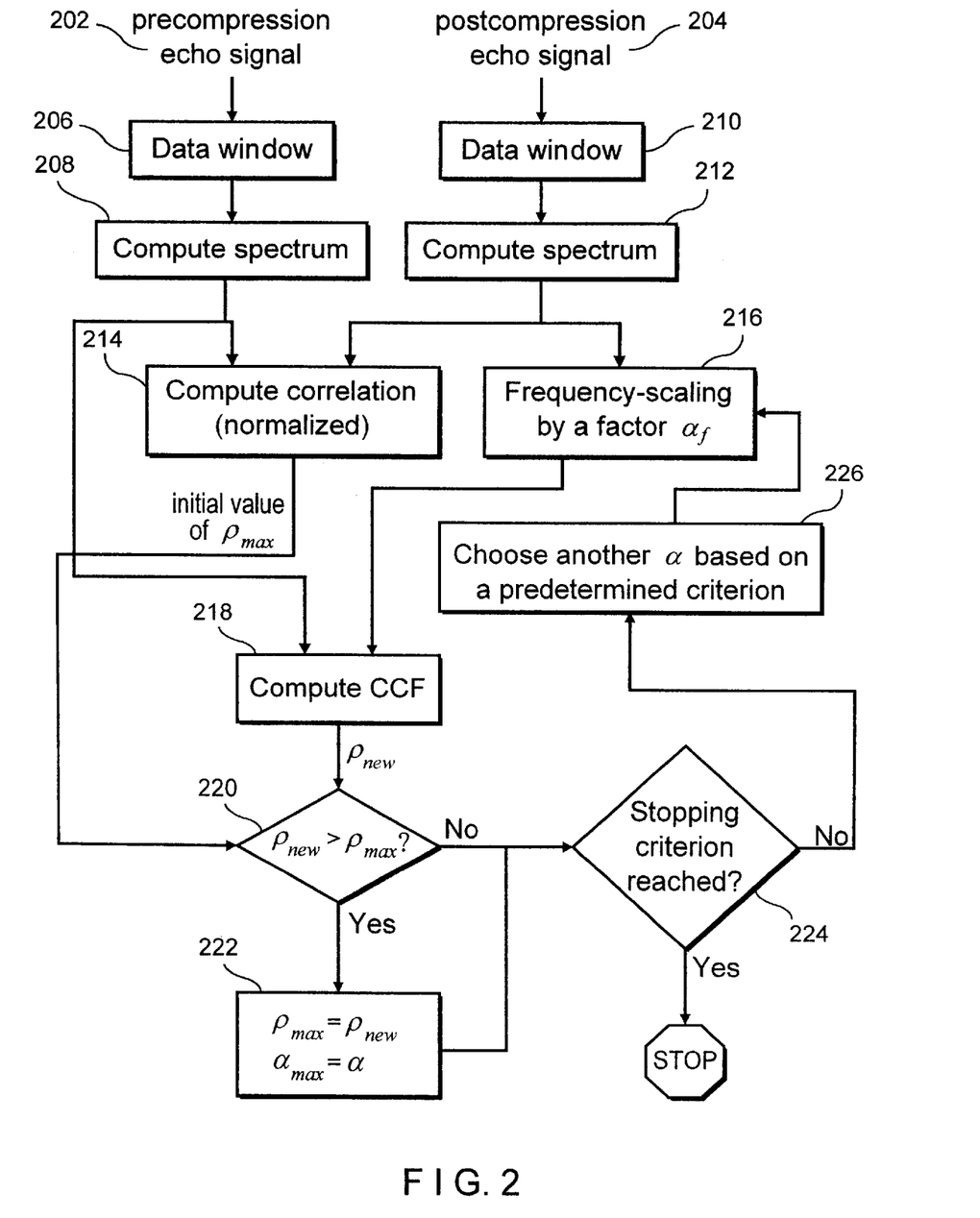
FIG. 2 is a flow-chart illustrating a method for spectral strain estimation.

The process of spectral strain estimation (step 120) involves determining the value of a frequency scaling factor for the post-compression spectra that maximizes the correlation with the pre-compression spectra. The scaling factor which maximizes the correlation, $\rho_{max}$, also characterizes the local tissue strain. FIG. 2 is a flow-chart further illustrating the spectral strain estimation process of step 120. In FIG. 2, it is assumed that pre-compression echo signal data 202 and post-compression echo signal data 204 have been acquired using an ultrasound elastography method. The time-domain pre-compression echo signal 202 is analyzed at a particular data window (step 206) and a pre-compression spectrum is computed, such as by employing a Fourier transform of the windowed pre-compression echo data (step 208). Similarly, corresponding post-compression spectrum is also computed (step 212) from post-compression echo signal data 204 at the corresponding data window (step 210). It will be appreciated that the process will be described only for a single data window (e.g., time segment of the temporal data) and that the process is repeated for each data window until the entire dataset of the echo signal data is analyzed and an elastogram is produced.

An initial correlation value is calculated between the pre-compression spectrum and the post compression spectrum (step 214). Step 214 need only be performed once as this initial correlation value is used only as an initial value of the maximum correlation value and is subsequently replaced during further processing as described below.

The spectrum of the post-compression data is frequency scaled by a frequency-scaling factor $\alpha_f$ (step 216). The initial value of the scaling factor can be assigned a predetermined value, which can be based on the applied compression value. The pre-compression spectrum and the frequency-scaled post-compression spectrum are then used to compute a cross-correlation function (CCF) to determine a value of the correlation $\rho_{new}$ between the frequency scaled post compression spectrum and the pre-compression spectrum (step 218).

The cross-correlation factor $\rho_{new}$ from step 218 is then compared to the current maximum value of the correlation factor $\rho_{max}$ in step 222. As set forth above, the initial value of $\rho_{max}$ is determined in step 214. If in step 222, the cross-correlation factor $\rho_{new}$ is larger than the current maximum value $\rho_{max}$, the value of $\rho_{max}$ is updated to equal $\rho_{new}$ (step 222). Also in step 222, the frequency-scaling factor which yields maximum correlation, $\alpha_{max}$, is set to the value of the current scaling factor $\alpha_f$ which was used to scale the post-compression spectrum in step 216. The new value of $\alpha_{max}$ is compared to a predetermined stopping criterion to determine whether an acceptable value has been reached (step 224). In case that such a criterion has not been reached, a new value of $\alpha_f$ is selected (step 226). The selection of a new value of $\alpha_f$ is discussed in more detail below with respect to FIG. 3. After a new value for the scaling factor is selected, control returns to step 216 and steps 216 through 226 are repeated until the predetermined criterion is reached (step 224). Once the predetermined criterion is reached, the value of $\alpha_{max}$ can be used to estimate tissue strain at the selected data window location ($\epsilon = 1 - \alpha_{max}$). The process of FIG. 2 is repeated for each data window of the echo signal data.

The determination of a frequency scaling factor which maximizes correlation as described in connection with FIG. 2 offers processing advantages over the calculation of scaling factors for the echo signal data in the time domain. Once such advantage is that a correlation search that is generally required in time-domain adaptive stretching because of the likelihood of a nonzero time delay existing between data segments in the pre-compression and post-compression signals is not generally required in the spectral domain (correlation computed only at zero lag).

Figure 3:
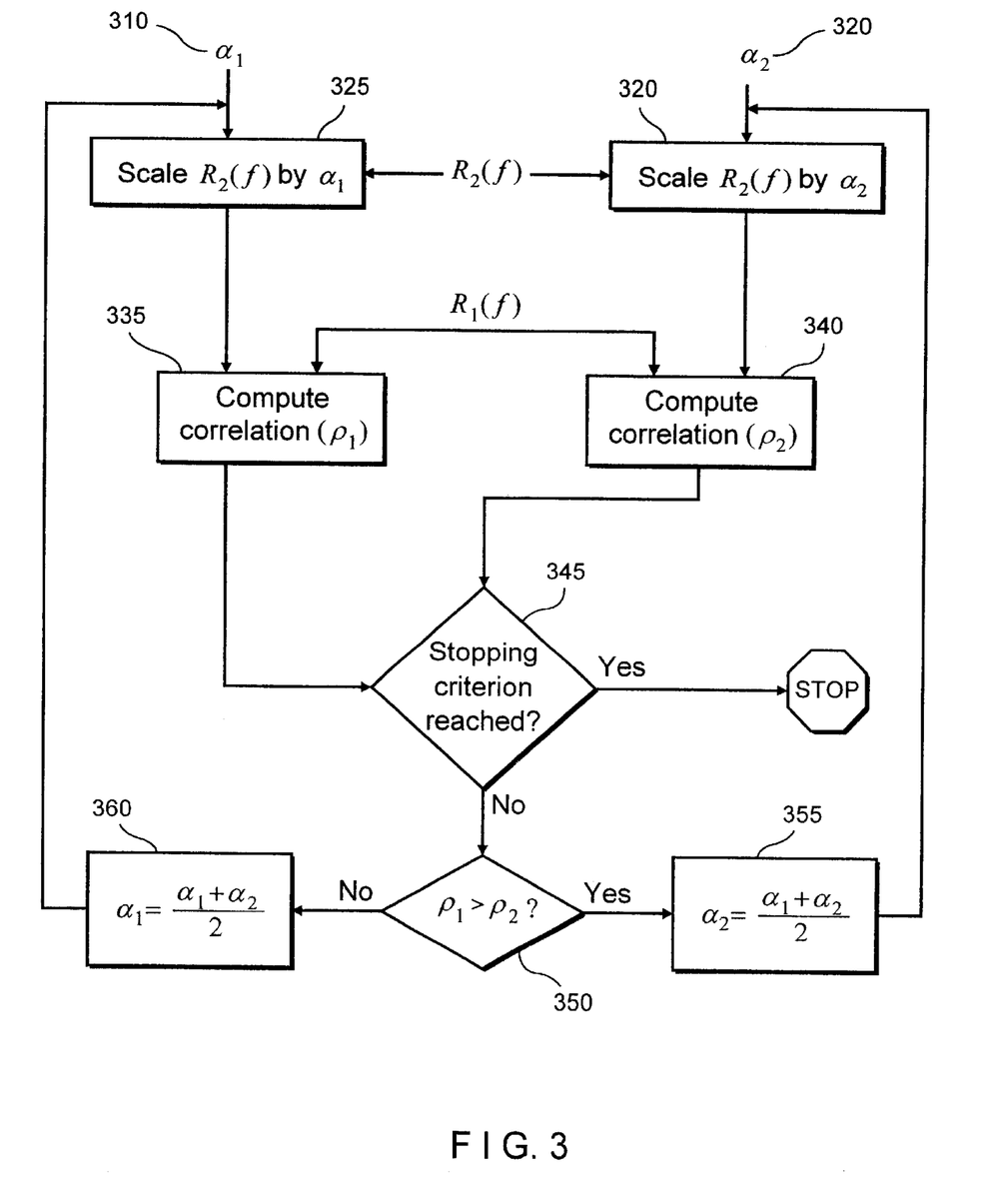
FIG. 3 is a flow-chart illustrating a method for performing a binary search for estimating a frequency scaling factor.

The selection of a new value for the scaling factor in step 226 can be estimated using an exhaustive search which is computationally extensive. A preferred method is to use a binary search method, which is illustrated in the flow chart of FIG. 3. FIG. 3 is a flow-chart of a binary search method for choosing the next value of a frequency scaling factor, such as in step 226 of FIG. 2. Referring to FIG. 3, two potential values for the scaling factor are selected, $\alpha_1$ 310 and $\alpha_2$ 320. Initial values (such as in step 214, FIG. 2) can be selected arbitrarily or from the results of an initial coarse search using a small number of equally spaced scale factors. The use of an initial coarse search is preferred as this reduces the possibility of converging to a value which is a false maximum.

The post-compression signal $R_2(f)$ is frequency scaled by the first scaling factor value (step 325) and also by the second scaling factor value (step 330). A first correlation value $\rho_1$, is calculated from the first scaled value of the post-compression spectrum and the pre-compression spectrum in step 335. Similarly, a second correlation value $\rho_2$ is calculated from the second scaled value of the post-compression spectrum and the pre-compression spectrum in step 340. The two correlation factors are compared to determine whether the difference in the values $\rho_1$ and $\rho_2$ have converged to within a predetermined value (step 345). If so, the binary search method terminates and the current value of $\alpha_1$ 310 or $\alpha_2$ 320 can be selected as the new value for the scaling factor in step 226. If the predetermined stopping criterion has not been reached, the values of the correlation factors are compared (step 350). If the value of the first correlation factor exceeds the value of the second correlation factor, the current value of the first scaling factor is retained and the value of the second scaling factor is assigned a value equal to the midpoint of the first and second scaling factors (step 355). If the value of the first correlation factor is less than the value of the second correlation factor, the current value of the second scaling factor is retained and the value of the first scaling factor is assigned a value equal to the midpoint of the first and second scaling factors (step 360). Steps 350 through 360 result in the retention of the scaling factor producing the larger correlation value and the search interval being halved. The process repeats from steps 325 and 330 until a predetermined stopping criterion is reached in step 345.

Figure 4:
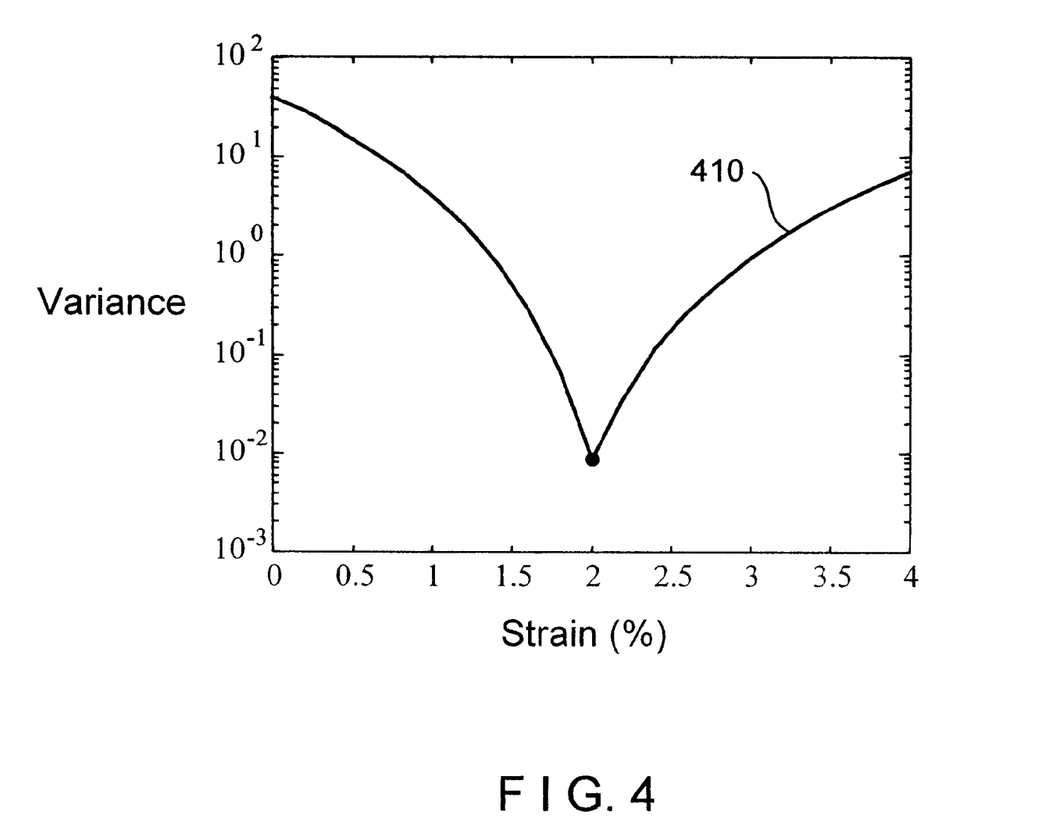
FIG. 4 is a Cartesian graph presenting variance of spectral ratio as a function of frequency scaling factor.

The spectral strain estimation process of FIG. 2 estimates the strain based on a frequency-scaling factor that maximizes the correlation between the pre-compression spectrum and the frequency scaled post-compression spectrum. An alternative method for computing strain is to divide the frequency scaled post-compression echo power spectrum with the pre-compression echo power spectrum and varying the scaling factor to minimize the variance of the result. Magnitude spectrum can also be used instead of power spectrum. FIG. 4 is a graph which illustrates the variance of the ratio between the scaled post-compression echo spectrum and the pre-compression echo spectrum; frequency-scaling factors were varied corresponding to 0 to 4% strains. Referring to FIG. 4, the variance 410 reaches its minimum when the frequency-scale factor matches the exemplary true strain of 2%. Hence, the frequency-scale factor that minimizes the variance of spectral ratio 410 can be used for estimating strain. The process of estimating strain by minimizing the variance of the ratio of the scaled post-compression spectrum and the pre-compression spectrum closely follows that depicted in FIG. 2, except that a variance of a ratio is minimized rather than maximizing a correlation.

The calculation of the variance can be less processor intensive than the process of determining the maximum correlation. However, since the process of minimizing the variance requires a step of dividing pre-compression and post-compression echo power spectra, a potential problem can arise if the value of the denominator approaches zero. This can be avoided by processing the spectrum in a defined portion of the bandwidth, such as a 15-dB bandwidth of the spectra may be used.

The deviation in the ratio of the pre-compression spectrum and the frequency shifted post-compression spectrum from smooth behavior can be approximately estimated from its variance. However, even a smooth variation may cause the variance to be nonzero. An approach preferred to straight variance calculation is to first smooth the ratio, subtract the smoothed function from the original ratio, and then compute the variance of the result.

Figure 5:
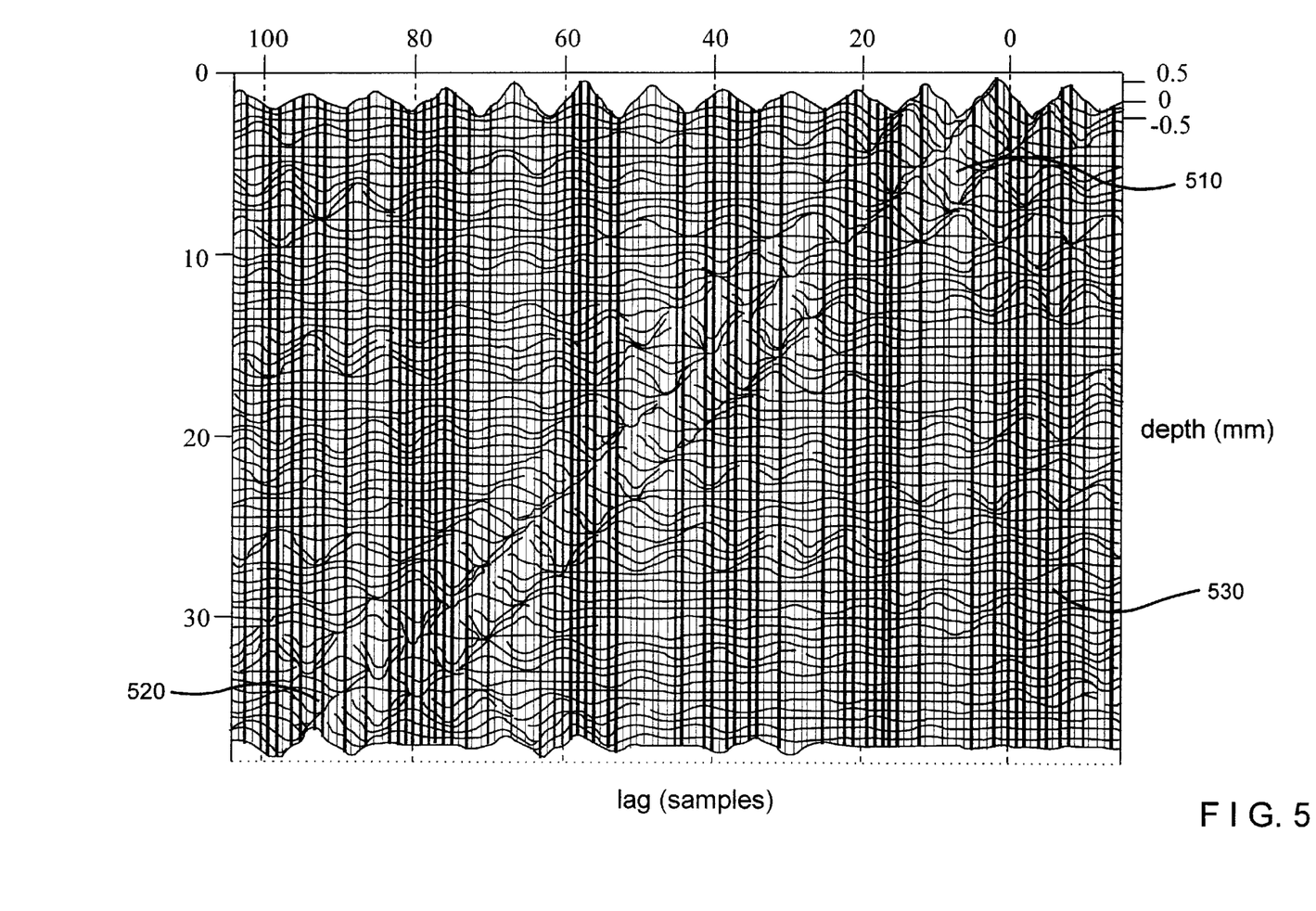
FIG. 5 is an illustrative diagram presenting a radio-frequency correlation as a function of depth.

The correlation tracking step 115 (FIG. 1) will now be described in further detail. Displacements (depth-dependent) between the pre-compression and post-compression data can be estimated from the location of peaks of correlation functions (such as 1-D and 2-D RF correlation functions). An example of this is illustrated in the graph of FIG. 5 of RF correlation function versus depth (depth being varied by a sliding window). As illustrated in FIG. 5, the use of such correlation functions results in both a number of true peaks 510 corresponding to true displacement and spurious peaks 530 (not corresponding to true displacement). The presence of the spurious peaks 530 introduces ambiguity in the displacement estimates which needs to be resolved.

The present method resolves ambiguities in the correlation data by tracking such peaks in a group, rather than individually and applying other rules to eliminate false peaks from the data.

FIG. 5 is a graph illustrating exemplary echo signal data from a finite element analysis (FEM) simulation of a rectangular block containing stiff cylindrical inclusions subjected to large externally applied strains of 4%. The one-dimensional RF correlation functions between pre- and post-RF echoes are determined using sliding windows. In this example, a window size is 2 mm, a window shift increment is 0.5 mm. In this example, the "true" correlation peaks 510 lie along a nearly diagonal line, permitting a rejection of most, if not all, spurious peaks 530. In addition, envelope and temporal stretching methods can also be used to eliminate erroneous peaks 530. Correlation peaks 510 can similarly be tracked in the lateral direction by plotting correlation functions vs. lateral position at a constant depth.

There may still be two or more combinations of peaks which are plausible, which result in undesirable ambiguity. Ambiguities in such situations can be resolved by using the following criteria, or rules set: (1) shifting between correlation peaks at consecutive depths is normally small because of motion continuity; (2) false peaks are in error by integer multiples of a wavelength at the ultrasonic center frequency; (3) peaks of envelope correlation are typically less precise but much more resistant to false peak errors compared to RF correlation, when envelope and RF correlation peaks do not match, envelope correlation peaks, especially when they are high ($\approx 1$), can be used to correct false peaks; and (4) many true peaks (both RF and envelope) can be identified from their high values ($\approx 1$), especially at resolvable boundary/landmarks, which are present in most cases. These peaks will impose constraints, similar to boundary conditions, on our estimates. From a plausible combination of correlation peaks, only one will be consistent with the motion of these landmarks. This can be used to eliminate ambiguities that are inconsistent with this displacement. These rules are not hierarchical and can be applied in any order to resolve ambiguities in determining which groups of correlation peaks represent true correlation. The method is described for a 1-D correlation analysis. However, it is believed that the method will work better if 2-D correlation analysis is performed as opposed to 1-D for estimating displacements. Then the above procedure to correct false peaks will be applied in 2-D (lateral and axial) as well.

The butterfly search of step 122 (FIG. 1) can be used for tracking complex motion and computing strains from estimated displacements. The butterfly search method is designed to track the axial movement of a group of scatterers between data frames and is described in the article "The butterfly search technique for estimating blood velocity" by Alam et al., IEEE, Ultrasound Med. Biol., vol. 21, No. 5, pp. 657–670, 1995, which is hereby incorporated by reference in its entirety. When a scatterer moves, it affects both the phase and time delay of RF echoes. The butterfly search method makes use of the fact that a particular inter-frame scatterer movement is associated with a unique combination of phase and time delay over multiple data frames. The butterfly search may help identify a delay trajectory where this unique combination of phase and time delay is best satisfied. This method is especially well suited for accurate delay estimation in the presence of decorrelation because it uses the combination of delay and phase change instead of only one of them.

The originally described butterfly search assumes a constant rate inter-frame scatterer displacement. However, inter-frame scatterer displacement does not have to be constant if digitized echoes from the boundary of the tissue can be clearly identified to reliably track surface movement. In this case, these measured boundary displacements may be incorporated so that the intra-frame displacement d is no longer a constant, but a function of n. In such a case, butterfly lines may have forms different from straight lines. In scaling d this way, it may be assumed that the tissue is in the linear elasticity region, so any change in surface displacement linearly affects local displacements. The butterfly search also may be adapted for 2D-motion estimation.

Figure 6A:
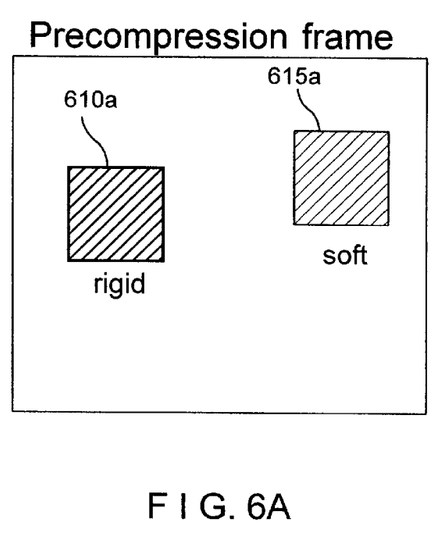
FIGS. 6A and 6B are pictorial diagrams illustrative of a correlation search performed by moving a 2-D window of pre-compression data over 2-D post-compression data.
Figure 6B:
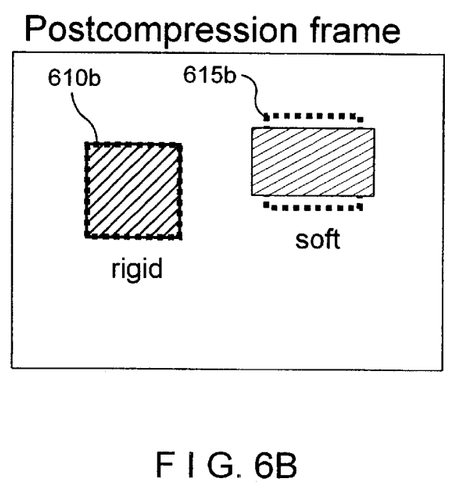

The step of detecting quasi-rigid motion using a maximum correlation magnitude (step 125, FIG. 1) will now be discussed in further detail. FIG. 6A illustrates an exemplary rigid or semi-rigid body 610a and a soft body 615a within a tissue prior to compression. Such a quasi-rigid body 610a can represent certain stiff cancerous tissues, implanted radioactive brachytherapy seeds which are used for cancer treatment and the like. In the presence of an external compression, such as the compressive force applied during elastography, the quasi-rigid body 610a tends to move to a new position within the tissue as a unit while experiencing little deformation, as illustrated in 610b in FIG. 6B. By contrast, the soft body 615a experiences both displacement and substantial deformation in the post-compression frame, as illustrated by 615b in FIG. 6B. Because the quasi-rigid objects are not subject to deformation, such objects may be tracked by employing correlation searches that involve moving a two-dimensional window of pre-compression data, including body 610a, through the 2-D post-compression data. Because there is little deformation, the correlation value in the window of post-compression data which includes the body 610b will be close to unity whereas the correlation in other windows that include softer objects of the body 615 will be significantly less than unity. Thus, the magnitudes of the cross-correlation between these 2-D areas can be used as an index of structural similarity and thus relative stiffness.

Figure 7:
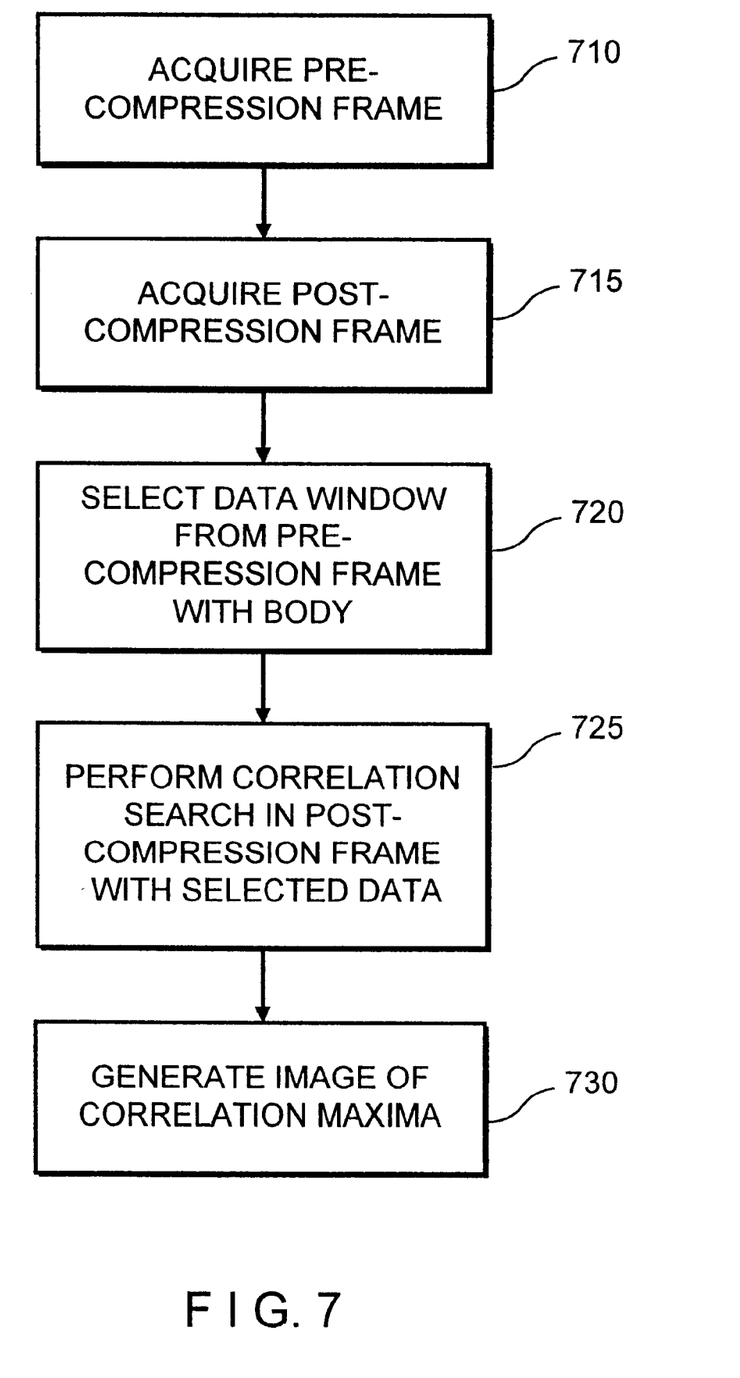
FIG. 7 is a flow chart illustrating a process for estimating strain and tracking quasi-rigid objects using a maximum correlation-magnitude technique.

FIG. 7 is a flow chart which illustrates the process of estimating tissue strain using a maximum correlation magnitude for quasi-rigid motion (step 125, FIG. 1). In step 710, pre-compression data is acquired and presented as a frame of 2-D pre-compression elastography data. Similarly, in step 715, post-compression data is acquired and presented as a frame of 2-D post-compression elastography data. A data window is selected from the pre-compression frame (step 720). Correlation searches are then performed by moving the data window from step 720 over the 2-D post-compression elastography data and the value of correlation maximums is determined (step 725). An image of correlation maximums can be generated by moving the 2-D data windows (step 720). This method identifies and tracks quasi-rigid bodies and also provides a semi-quantitative indicator of tissue strain.

The processes described herein provide improved signal processing for generating elastograms. These techniques are of particular value when undesired motions may be induced while acquiring elastographic data, such as when manual compression is being used. It will be appreciated that while described in the context of the hierarchical signal processing method, several of the processing methods described herein can be used independently of the others to achieve improved elastograms.

The invention has been described in connection with certain preferred embodiments. It will be appreciated that certain changes and modifications may be made by those skilled in the art without departing from the scope and spirit of the invention which is set forth in the appended claims.

What is claimed is:

1. A method of estimating tissue strain, comprising:
   a) transmitting ultrasonic signals into tissue and detecting first reflected signals;
   b) compressing said tissue to cause tissue strain;
   c) transmitting ultrasonic signals into said compressed tissue and detecting second reflected signals;
   d) computing first and second Fourier Transforms of said first and second reflected signals;
   e) frequency scaling one of said first and second Fourier Transforms;
   f) deriving a correlation signal of said scaled Fourier Transform and said other Fourier Transform; and
   g) determining tissue strain from the frequency scaling factor representing a maximum of said correlation signal.

2. The method of claim 1, wherein the frequency-scaling factor representing said maximum of said correlation signal is estimated using a binary search.

3. A method of estimating tissue strain, comprising:
   a) transmitting ultrasonic signals into tissue and detecting first reflected signals;
   b) compressing said tissue to cause tissue strain;
   c) transmitting ultrasonic signals into said compressed tissue and detecting second reflected signals;
   d) converting said reflected signals to the spectral domain;
   e) low-pass filtering said first and said second reflected signals;
   f) applying a scaling factor to frequency scale one of said first and said second filtered reflected signals;
   g) deriving a correlation signal of said time-scaled filtered reflected signal and said other signal; and
   h) altering the scaling factor to maximize the correlation signal;
   i) using the scaling factor which maximizes the correlation signal as an estimate of tissue strain.

4. A method of estimating tissue strain, comprising:
   a) transmitting ultrasonic signals into tissue and detecting first reflected signals;
   b) compressing said tissue to cause tissue strain;
   c) transmitting ultrasonic signals into said compressed tissue and detecting second reflected signals;
   d) computing first and second Fourier Transforms of said first and second reflected signals;
   e) frequency scaling one of said first and second Fourier Transforms;
   f) computing the variance of a ratio of said scaled Fourier Transform and said other Fourier Transform; and
   g) determining tissue strain from the frequency scaling factor representing a minimum of said variance.

5. The method of claim 4, further comprising the steps of:
   a) smoothing said ratio;
   b) subtracting a smoothed function from said ratio; and
   c) computing a variance between said smoothed ratio and said non-smoothed ratio.

6. A method of estimating tissue strain, comprising:
   a) transmitting ultrasonic signals into tissue and detecting first reflected signals;
   b) compressing said tissue to cause tissue strain;
   c) transmitting ultrasonic signals into said compressed tissue and detecting second reflected signals;
   d) determining a set of correlation functions between said first and said second reflected signals;
   e) computing correlation peaks corresponding to said correlation functions;
   f) tracking correlation peaks of said set of correlation functions in a group to eliminate false peaks; and
   g) determining tissue strain from the tracked group of correlation peaks.

7. The method of claim 6, wherein said step of computing correlation peaks further comprises computing envelope peaks corresponding to said set of correlation functions.

8. The method of claim 7, wherein said step of determining said set of correlation functions further comprises temporally stretching said second reflected signals to eliminate erroneous peaks.

* * * * *